United States Patent [19]
Tarver

[11] Patent Number: 6,030,222
[45] Date of Patent: Feb. 29, 2000

[54] DYE COMPOSITIONS AND METHODS FOR WHITENING TEETH USING SAME

[76] Inventor: Jeanna G. Tarver, 1248 E. 600 S., Bountiful, Utah 84010

[21] Appl. No.: 09/203,007

[22] Filed: Dec. 1, 1998

[51] Int. Cl.[7] .................................................. A61C 5/00
[52] U.S. Cl. ...................... 433/217.1; 433/215; 433/216; 424/53
[58] Field of Search ................................... 433/215, 216, 433/217.1; 424/53

[56] References Cited

U.S. PATENT DOCUMENTS

| | | | |
|---|---|---|---|
| 3,936,385 | 2/1976 | Cheng | 424/53 |
| 4,097,994 | 7/1978 | Reaville | 433/217.1 |
| 4,150,106 | 4/1979 | Assal et al. | 424/7 |
| 4,537,778 | 8/1985 | Clipper et al. | 424/53 |
| 5,078,988 | 1/1992 | Lin et al. | 424/49 |
| 5,180,575 | 1/1993 | Ha et al. | 404/49 |
| 5,433,941 | 7/1995 | Patel | 424/50 |
| 5,718,886 | 2/1998 | Pellico | 433/215 |
| 5,766,011 | 6/1998 | Sibner | 433/215 |
| 5,785,527 | 7/1998 | Jensen et al. | 433/215 |
| 5,846,570 | 12/1998 | Barrow et al. | 424/616 |

*Primary Examiner*—John J. Wilson
*Assistant Examiner*—Patrick A. Hilsmier
*Attorney, Agent, or Firm*—Berne S. Broadbent; Dale E. Hulse

[57] ABSTRACT

Compositions, methods and systems for whitening teeth. A whitening composition is applied to off-white or yellowish teeth in order to hide or mask the inherent underlying natural tooth color to yield whiter looking teeth. The whitening composition includes a complementary dye that, when absorbed by a tooth, will cause the tooth to reflect a color of light that is whiter than the natural or initial color reflected by the tooth. The tooth whitening composition may comprise a toothpaste that is applied like any conventional toothpaste in order to achieve whitening without significant alteration of a person's daily routine. Alternatively, the tooth whitening composition may be adapted for direct application onto the teeth in a more concentrated form, such as by means of a syringe, tooth cleaning paste, or cotton swab. The tooth whitening compositions can be used instead of, or in addition to, dental bleaching compositions in order to achieve whiter teeth while reducing or eliminating tooth sensitivity caused by some bleaching regimens. The inventive whitening compositions may also be used in conjunction with a bleaching composition in order to maintain whiter teeth for a larger period of time before undertaking subsequent bleaching regimens.

20 Claims, 1 Drawing Sheet

DYE COMPOSITIONS AND METHODS FOR WHITENING TEETH USING SAME

BACKGROUND OF THE INVENTION

1. The Field of the Invention

The present invention is in the field of cosmetic tooth whitening. More particularly, the present invention is in the field of applying a whitening composition that includes one or more complementary dyes to a person's teeth using an appropriate carrier or applicator in order to make the teeth appear more white.

2. The Relevant Technology

In the last decade, tooth bleaching has become extremely popular as more and more people realize the cosmetic benefits of having whiter teeth. There are presently a wide variety of tooth bleaching regimens available. Some are intended strictly for use in a dentist's office, such as laser bleaching, while others comprise home bleaching kits that can either be purchased from a dentist or from mail order television advertisements. Some bleaching regimens utilize compositions having relatively low concentrations of bleaching agent and may take weeks or even months to complete. Other more concentrated and powerful bleaching compositions used in dental offices can show more immediate results.

Although tooth bleaching regimens have found widespread acceptance, they are not without problems. First of all, the bleaching compositions and associated equipments and/or dentist labor costs are relatively high. Laser bleaching procedures performed by dentists at the dental office can cost hundreds, even thousands, of dollars depending on the number of teeth and the severity of staining that must be bleached out. Although cheaper than laser bleaching, home bleaching regimens purchased from dentists can cost hundreds of dollars. Even mail order bleaching regimens from television advertisements can cost upwards of a hundred dollars or more.

Another problem associated with tooth bleaching is the application of peroxide bleaching agents onto the teeth, which have reportedly caused increased tooth sensitivity in some people. Some have even reported moderate to severe pain. One theory is that increased sensitivity and pain result from the bleaching agent working its way through pores which naturally occur in teeth and into the pulp chamber. Others have posited that certain carriers can cause teeth to become somewhat desiccated or dehydrated, which can cause increased internal fluid pressure and pain within the pulp chamber.

In response to reported cases of increased tooth sensitivity, some manufacturers of tooth bleaching compositions have tried alternative solvents within the carrier in order to reduce the dehydrating effects of the bleaching composition. Others have prepared desensitizing compositions intended to offset the painful effects of tooth bleaching.

While the foregoing remedial steps have helped to reduce tooth sensitivity, they have not eliminated or reduced the root cause of sensitivity, which is the use of peroxide-based bleaching agents as the sole means for whitening. If anything, the use of desensitizing agents has allowed for the use of even harsher and more concentrated bleaching compositions.

Accordingly, what are needed are dental compositions and methods for whitening a person's teeth which eliminated, or at least reduced, the need for applying bleaching compositions to a person's teeth.

In addition, what are needed are compositions and methods for whitening a person's teeth which did not result in increased tooth sensitivity or pain.

It would be a further advancement in the art to provide compositions and methods for whitening teeth that could increase tooth whiteness above and beyond what is possible using bleaching compositions alone.

Such compositions and methods for whitening teeth are disclosed and claimed herein.

SUMMARY AND OBJECTS OF THE INVENTION

The present invention relates to dental compositions and methods for whitening teeth. The primary whitening agent within the inventive dental compositions comprises a complementary color which, when used to treat discolored teeth, acts to mask the color of the teeth so that whiter teeth are perceived. The result is the ability to whiten teeth while eliminating, or at least reducing, the need for bleaching agents in order to obtain and maintain whiter looking teeth.

Depending on the thickness and opacity of the enamel, as well as the color of the underlying dentin, the natural color of a person's teeth can vary greatly between white, off-white, yellowish-white, and yellow. In addition, teeth can become discolored from tea, coffee, antibiotics, and certain foods. Whereas toothpastes and polishes can remove superficial staining, they are incapable of appreciably changing the inherent color of a person's teeth. Bleaching has more recently been exployed to attack and bleach natural yellowish pigments found within teeth as well as superficial stains.

The compositions of the present invention take advantage of the concept of color cancellation in order to mask or alter the initial tooth color in order for the teeth to appear whiter. For example, television and computer screens utilize a matrix of pixels, with each pixel emitting only one of three primary emission colors: cyan blue, magenta, and yellow-green. By emitting different intensities of the three primary colors, shades of every color can be produced, even white, which is the combination of all emitted light wavelengths. The inventive compositions utilize this same principle (i.e., the emission of multiple colors that blend to form whiter light) in order for the teeth to reflect whiter light even though the teeth may have originally reflected light of a more yellowish tint.

The complementary color that can blend with most, if not all, off-white and yellowish-tinted teeth to yield whiter looking teeth will be in the range from violet to blue-violet. Typically, the complementary color can be added to the person's teeth in the form of a dye that is somewhere in the range from violet to blue-violet. Because a person's own teeth can vary from tooth to tooth, it may be necessary to treat each tooth with different shades or intensities of different complementary dyes in order for all the teeth to appear to have the same shade of white.

Nevertheless, it will be possible in many cases to simply use an average of various complementary colors on the teeth as a whole, which has been found to be a shade of bluish-violet. In other words, the most typical complementary color for whitening teeth will constitute a violet dye to which a small amount of blue dye has been added. Nevertheless, it should be understood that any particular dye or combinations of dyes that can cause teeth to reflect a whiter color compared to the natural or initial tooth color is certainly within the scope of the invention.

In a preferred embodiment, the complementary dyes are blended with a carrier in order to dilute the dye to a desired concentration and to yield a composition having a desired consistency and ability to be absorbed by the teeth. It is generally desirable for the dye to offset the underlying tooth color without causing the surrounding oral tissues to become stained in an unsightly manner. In many cases, the carrier can simply be a toothpaste formulation that is brushed onto a person's teeth during daily brushing. This causes the complementary dye to be applied to the teeth on a constant basis with virtually no change in the person's daily routine. The complementary dyes can be included within pastes used by dentists and hygienists to professionally clean a patient's teeth. Higher concentrations of the complementary dye within an appropriate carrier can also be applied at high strength using an applicator or other application means, such as a syringe or cotton swab, in order to impart a more immediate and striking change in the color of the person's teeth.

The exact mechanism by which a tooth is able to absorb or take the complementary dye is not entirely known. Nevertheless, it is known that teeth have microscopic pores in the enamel surface. One explanation is that the complementary dyes are able to become embedded within these pores. Because the microscopic pores are widely scattered throughout the tooth, the dye can be substantially uniformly distributed over the entire tooth surface.

As light is reflected by the tooth, much of the light reflected by the tooth will normally constitute white light, which actually includes light of all colors. However, yellowish pigments found within some teeth can cause teeth to reflect yellowish colors in addition to white light, which can yield teeth that reflect a yellowish-white tint. By adding a complementary color to the tooth, such as by means of the tooth absorbing a complementary dye, the light reflected by the treated tooth will include rays of the complementary color as well as yellowish light rays. The light rays of the complementary color combine with and offset the yellowish light rays to yield a blend of light rays that are perceived by the viewer as constituting white light, or at least light that is whiter than the original off-white, yellowish-white, or yellowish tones.

Although the compositions of the present invention are able to mask or blend with yellowish tones to produce whiter looking teeth, it is certainly within the scope of the invention to augment the whitening effect using any known bleaching or whitening composition known in the art. Certain colors may not respond as well as others to the masking effect of the complementary dyes and may require pre-bleaching in order for the teeth to achieve their whitest possible look. The inventive compositions can be used in conjunction with conventional bleaching regimens known in the art in order to further augment, intensify, or prolong the desired whitening effect. Moreover, stable dyes in the range from violet to violet-blue can be added directly to bleaching compositions to further whiten teeth.

In view of the foregoing, it is an object of the invention to provide dental compositions and methods for whitening a person's teeth which eliminate, or at least reduce, the need for applying bleaching compositions to a person's teeth.

In addition, it is an object to provide compositions and methods for whitening a person's teeth which do not result in increased tooth sensitivity or pain, or which can at least assist in maintaining tooth whiteness while using less bleaching composition.

It is a further object of the invention to provide compositions and methods for whitening teeth that can increase tooth whiteness above and beyond what is possible using bleaching compositions alone.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawing depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
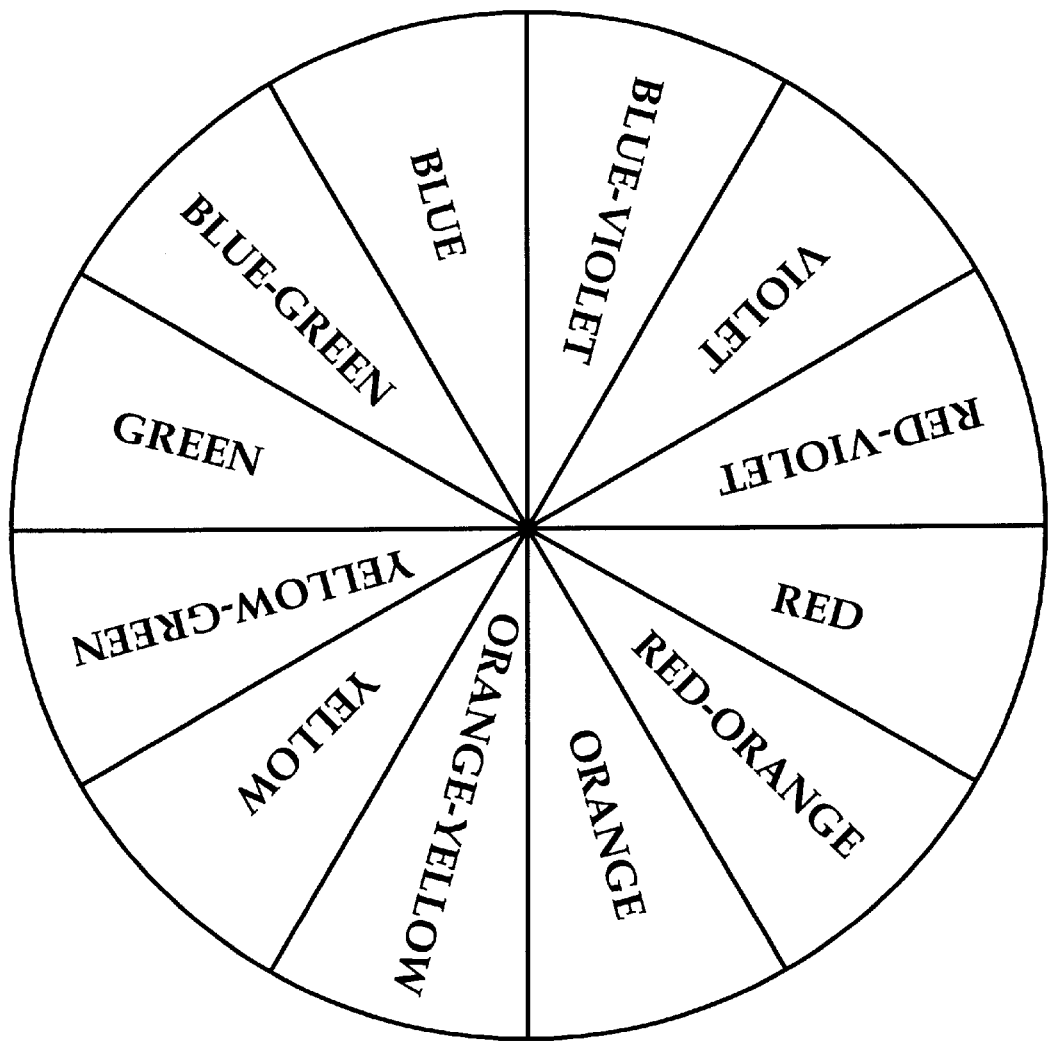
FIG. 1 is a circular chart or color wheel showing various colors of the spectrum and their associated complementary colors.

The present invention relates to dental compositions and methods for whitening teeth. The primary whitening agent within the inventive dental compositions comprises a complementary dye color which, when used to treat off-white and yellowish teeth, acts to mask yellowish and off-white colors of the teeth so that whiter teeth are perceived. The result is the ability to whiten teeth while eliminating, or at least reducing, the need to bleach teeth in order to obtain whiter looking teeth.

A typical healthy tooth consists of an enamel surface and a dentin sublayer beneath the enamel surface. The enamel surface comprises a highly calcified material that is preferably very hard and durable to allow chewing of a wide variety of foods. The dentin sublayer is also durable but is considerably softer than the enamel. In addition, dentin tends to have more of a yellowish hue compared to enamel, which tends to be white but which can also be somewhat clear or translucent, which can allow the yellowish tints of the dentin to show through the enamel.

Depending on the thickness, opacity and whiteness of the enamel, the color of a person's teeth can vary widely between various shades of white, off-white and yellow. Teeth can also accumulate plaque and tartar, which can further alter the color of the person's teeth. While over-the-counter toothpastes can remove accumulations of plaque and tartar, they are incapable of appreciably altering the natural color and opacity of enamel. Although a large number of whitening and polishing toothpastes have made claims of whitening teeth, such formulations are virtually incapable of altering the underlying color of a person's teeth beyond removing plaque and tartar. The same is true for teeth cleaning procedures routinely carried out at the dental office—the inherent color of the person's teeth remains largely unchanged after plaque and tarter are removed.

A. Complementary Dyes

Most teeth that are not white will reflect light that is perceived to be off-white, yellowish-white, or even yellowish. In general, in order for a dye that is absorbed by off-white or yellowish teeth to emit whiter looking light it will be necessary to select a dye of a complementary color that when combined with yellowish tints, will cancel out the yellowish tint such that whiter light is perceived. Reference is now made to FIG. 1, which is a color wheel or chart showing the various colors of the spectrum and their interrelationship as complementary colors. Colors that are directly opposite to each other along the wheel are "complementary" such that combining lighter shades of the two emitted colors will yield whiter looking light than either of the two colors by themselves. Of course, it helps that the color emitted by even discolored teeth is predominantly white, which includes all colors with only minor amounts of excess yellowish or off-white tints being emitted. This makes it easier to cancel out these excess yellowish tints by means of a complementary dye.

In particular, it has been found that incorporating a small amount of violet or bluish-violet dye to a tooth tends to offset the yellowish tints to produce a whiter looking tooth. In most cases, the complementary dye that is most preferred will be bluish-violet, with violet predominating. Nevertheless, due to the wide variety of possible tooth colors, it is certainly within the scope of the invention to select any appropriate color that, when applied to a person's teeth, will cause the teeth to emit whiter looking light.

Accordingly, any appropriate dye that can be absorbed by teeth to yield whiter looking teeth is within the scope of the invention. In a preferred embodiment, the dye can be dispersed or dissolved within a hydrophilic solvent (discussed hereinafter) in order to be compatible with the aqueous environment surrounding a person's teeth. Dyes within the scope of the present invention are preferably not harmful if swallowed although it is preferable to apply the dyes to a person's teeth and then expel any excess dye from a person's mouth subsequent thereto. Nevertheless, because the dyes will be placed within a person's mouth, and due to the possibility that some of the dyes might be ingested, it is preferable for the dyes to be edible, or at least not harmful for human consumption.

Preferred dyes within the scope of the present invention include confectionery dyes used in coloring foodstuffs. Good confectionery dyes that are safe for human consumption are manufactured by Wilton Enterprises, located in Woodridge, Ill. Violet and blue dyes manufactured by Wilton Enterprises included dyes dispersed in a mixture of water, corn syrup, sugar, modified food starch, agar and carrageenan gums, citric acid, and 1/10 of 1% sodium benzoate and potassium sorbate as preservatives. A wide variety of dye colors from Wilton Enterprises and other manufacturers are readily available from stores that sell confectionery colorants.

The exact shade of violet, blue-violet or combination of violet and blue dyes that will have the maximum whitening effect on a particular tooth will depend on the tooth color. Nevertheless, in those cases where it is appropriate to blend blue and violet dyes together the ratio of blue dye to violet dye will preferably be in a range from about 1:100 to about 10:1, more preferably in a range from about 1:20 to about 2:1, most preferably in a range from about 1:10 to about 1:2. It should be understood that these ranges are based on the use of dyes having particular shades of violet and blue obtained from Wilton Enterprises. Other violet and blue dyes having slightly different shades, intensities, solubilities and other variable properties may require different ratios in order to yield a dye mixture having the proper blend of violet and blue tints.

B. Carriers

In many cases it will be preferable to disperse the complementary dye or mixture of dyes within a carrier in order to adjust the concentration of the dyes. As set forth above, dyes sold by Wilton Enterprises were themselves dispersed in a carrier solution identified above in an unspecified amount. The amount of additional carrier that should be added to a particular dye will depend on the desired concentration of dye within the final whitening composition, as well as the intensity or strength of the dye being added to the carrier. The carrier can also yield a final tooth whitening composition having a desired rheology or consistency.

With the foregoing in mind, it is generally desirable for the whitening composition, and particularly the dye within the whitening composition, to offset the underlying tooth color without excessively staining the surrounding oral tissues for long periods of time. One of ordinary skill in the art will be able to test a particular dye concentration to determine if it will cause excessive staining of the surrounding tissues when used in a particular manner. In some cases, just a few drops of dye may be added to a tube of toothpaste. In other cases, the dyes may be applied full strength (with the understanding that confectionery dyes themselves include significant quantities of carriers in order to make the dyes fluid and readily soluble in foods).

One preferred class or range of carriers within the scope of the present invention comprises any toothpaste or other dentifrice intended for cleaning of a person's teeth. In this way, the complementary dyes can be applied to a person's teeth without affecting a person's daily routine. This allows a person to apply dye to discolored teeth anytime brushing is carried out. Moreover, toothpastes can include greatly varying concentrations of dye in order to provide for quicker or slower absorption of the complementary dye by the person's teeth.

Alternatively, the complementary dyes can be dispersed within nonabrasive liquid carriers such as water, alcohols, glycerin and other polyhydric alcohols, polyols, ketones, aldehydes, carboxylic acids, carboxylic acid salts, and amines. The foregoing liquid carriers tend to be hydrophilic, which aids in the absorption of the complementary dyes in the aqueous environment surrounding the teeth.

In addition, a number of gelling agents can be used to yield gels or more viscous liquids. These include, but are not limited to, polycarboxylic acids, polycarboxylic acid salts, polysaccharides, polysaccharide derivatives, proteins, protein derivatives, polyalkylene oxides, fumed silica, and the like. Nonabrasive compositions are preferred when applying the complementary dyes directly to a person's teeth using applicators other than toothbrushes or dental office cleaning cups.

In yet another embodiment, the complementary dyes can be mixed with pastes used by dentists and dental hygienists to professionally clean their patients' teeth. The deep scrubbing action of the teeth cleaning procedure can work the complementary dyes into the pores of a patient's teeth in order to carry out a tooth whitening procedure during routine teeth cleaning.

The type and concentration of solvents and other components within the carriers will preferably yield a whitening composition having a desired consistency so that the composition (1) can be applied to a person's teeth and remain there as desired, (2) can be absorbed by the teeth, and (3) can be easily removed in order to remove excess dye from the teeth and surrounding oral tissues. In general, it is preferable for the dye to penetrate within the pores in a manner that allows dye remaining on the tooth surfaces to be removed, while leaving the dye within the pores to yield a diffuse, but significant amount, of dye in order to offset the yellowish tints of a person's teeth. In general, the compositions should be viscous enough so as to not run off the teeth but not so viscous that penetration of the dyes into the person's teeth is prevented.

The concentration of the complementary dye can vary greatly, from one or a few drops (e.g., 1–15 drops) within a standard size tube of toothpaste (e.g., a 4 ounce tube), to full strength applications using an appropriate applicator. To make tooth whitening pastes, it may be appropriate to use from about 0.1% to about 50% of the complementary dye by volume of the whitening paste. It may be possible for the dye and associated carriers to supply the liquid fraction of such pastes, with the abrasives comprising the balance of the constituents. It will be appreciated that the a wide range of concentrations may work depending on the application procedure, the initial whiteness of the person's teeth, and the strength of the dyes being employed.

C. Treating Teeth With Tooth Whitening Compositions

The whitening compositions within the scope of the invention can be applied to a person's teeth in any manner so long as the yellowish or off-white tints are at least partially cancelled out to yield whiter looking teeth. As stated above, one preferred method of application is by means of a toothbrush, such as when a toothpaste composition including a complementary dye is employed. Nevertheless, it is certainly within the scope of the invention to utilize a toothbrush with abrasive and nonabrasive gels or liquids that do not technically qualify as toothpastes. One advantage of using a toothbrush is the ability to work the complementary dyes into the teeth by means of a scrubbing action in order to evenly and thoroughly coat a person's teeth. By the same reasoning, the complementary dyes can be scrubbed onto patients' teeth during routine teeth cleaning procedures.

In addition, the inventive dental compositions can be applied to a person's teeth by means of other applicators, such as a cotton swab commonly used for cosmetic hygienic purposes. Another useful applicator is a syringe that allows for careful coating of the teeth with the whitening compositions. It is certainly within the scope of the present invention to use any application means that can apply a desired amount of the whitening composition over a person's teeth while not excessively staining surrounding tissues.

In general, it will often be preferable to initially treat off-white or yellowish teeth with a more concentrated complementary dye formulation in order to impart a more immediate and striking change in the color of the person's teeth. Thereafter, tooth maintenance can be carried out by using less concentrated formulations, such as toothpastes that can be applied daily during normal tooth hygiene.

Whereas the whitening compositions within the scope of the invention can be used alone in order to whiten a person's teeth, they may also be used in conjunction with bleaching compositions. For example, a person may begin a whitening regimen by first bleaching his or her teeth in order to achieve a first level of whiteness. Thereafter, the teeth can be further whitened, or the whiteness attained by bleaching may be maintained, by means of the whitening compositions within the scope of the invention. In fact, it has been observed that the tooth whitening compositions of the present invention are capable of making white teeth appear even whiter due to the optical effect of violet and bluish dyes absorbed by the teeth.

Alternately, complementary dyes that are stable in the presence of tooth bleaching compositions can be added directly to such compositions in order to enhance their whitening effect. Suitable tooth bleaching agents for bleaching teeth include a wide variety of peroxides, an example of which is hydrogen peroxide.

The exact mechanism by which a tooth is able to absorb or take a complementary dye is not entirely known. Nevertheless, it is known that teeth have microscopic pores in the enamel surface. One explanation is that the complementary dyes are able to become imbedded within these pores. Because the microscopic pores are widely dispersed throughout the teeth, the dye can be substantially uniformly distributed over the entire tooth surface.

As light is reflected by the tooth white light will predominate as the reflected light. The yellowish light emanating from the yellowish pigment found within a person's teeth will blend with the bluish-violet light emitted by the complementary dye in order to yield whiter light that is reflected by the teeth. Thus, teeth that originally may have appeared off-white, yellowish-white, or yellow will reflect whiter light and thereby appear to be whiter.

D. Examples of the Preferred Embodiments

In order to more clearly illustrate the parameters of the inventive tooth whitening compositions within the scope of the present invention, the following examples are presented. Examples which have been actually been carried out are described in past tense, while hypothetical examples are listed in present tense. The following examples are intended to be exemplary and should not be considered to limit the scope of the present invention.

EXAMPLE 1

A whitening composition according to the present invention was prepared by mixing together 4 ounces of Crest® brand Fresh Mint Gel With Tarter Control with 8 drops of Wilton Enterprises® Violet dye composition. The dye composition was measured using a standard size medicinal eye dropper. The 8 drops of dye were determined to constitute approximately 0.5 ml, while the 4 ounces of toothpaste equaled about 112 ml. Thus, the concentration of added dye was about 0.5% by volume in this example. The toothpaste already included FD&C Blue No. 1 so no additional blue dye was added to the whitening composition. The violet dye composition included unspecified amounts of FD&C Red No. 3 and FD&C Blue No. 1 in a carrier solution that included water, corn syrup, sugar, modified food starch, agar and carrageenan gums, citric acid, and $\frac{1}{10}$ of 1% sodium benzoate and potassium sorbate as a preservative.

The whitening composition was applied to a person's teeth during a normal brushing routine and was found to cause a noticeable whitening of the person's teeth. The whitening composition was applied during normal brushing over a period of months on an experimental basis and was found to cause continued whitening of the person's teeth. At some point saturation was reached and further whitening of the teeth ceased. However, the level of whiteness attained to this point was maintained so long as the person continued to brush with the whitening composition.

EXAMPLE 2

A whitening composition according to the present invention was prepared by mixing together 4 ounces of Colgate® Whitening Toothpaste with Baking Soda and Peroxide with 6 drops of Wilton Enterprises® Violet dye and 1 drop of Wilton Enterprises® Blue dye. The dye was measured using a standard size medicinal eye dropper. The toothpaste was white and initially included no colored dyes. The violet dye was the same as that used in Example 1, while the blue dye composition included FD&C Blue No. 1 in a carrier solution that also included the same ingredients used in the violet dye. The concentration of dye within the toothpaste was about 0.4% by volume.

The whitening composition was applied to a person's teeth during a normal brushing routine and was found to cause a noticeable whitening of the person's teeth. The whitening composition was applied during normal brushing over a period of months on an experimental basis and was found to continue whitening the person's teeth. At some point saturation was reached and further whitening of the teeth ceased. However, the level of whiteness attained to this point was maintained so long as the person continued brushing with the whitening composition. The whitening composition of Example 2 was found to be superior in whitening ability compared to the whitening composition of Example 1 in terms of speed and intensity of whitening, although both compositions were able to whiten teeth well.

EXAMPLE 3

A mixture of violet and blue dyes having a ratio of 5:1 violet to blue dye was applied directly to a person's teeth using a cotton swab as an applicator. The dye mixture was left on the teeth for 2 minutes and then rinsed and scrubbed off using a toothbrush. The person's teeth exhibited immediate whitening such that a whiter shade of teeth were clearly observed.

EXAMPLE 4

The whitening compositions of Examples 1 and 2 were applied to a person's teeth subsequent to or during a tooth bleaching procedure in which the person's teeth were successfully bleached to a certain degree of whiteness. The whitening composition caused a noticeable brightening and further whitening effect such that whiter and bright teeth were perceived. Continued use of the tooth whitening compositions of Examples 1 and 2 maintained the increased whiteness and brightness of the person's teeth.

EXAMPLE 5

A mixture of violet and blue dyes having a ratio of 7:1 is mixed with tooth cleaning abrasive in order to form a professional tooth cleaning/whitening paste having a concentration of 10% by weight of the dye mixture. The tooth cleaning paste can be applied to a person's teeth during routine cleaning of a patient's teeth in a dental office in order for the complementary dye to be applied to the person's teeth. Depending on the type and initial color of the patient's teeth, various degrees of whitening may be obtained, although darker teeth may not noticeably whiten using this procedure.

EXAMPLE 6

Any of the foregoing whitening compositions are altered by adding a peroxide-based tooth bleaching agent, such as hydrogen peroxide, in order to form a dental whitening composition capable of both bleaching as well as applying a complementary dye to a person's teeth to enhance tooth whiteness. The dyes should be selected to be stable for at least a little while to allow bleaching of the teeth without complete destruction of the complementary dye. The whitening effect made possible by the peroxide-based bleaching agent is enhanced by the absorption of the complementary dye by the teeth.

E. Summary

The present invention provides dental compositions and methods for whitening a person's teeth which eliminate, or at least reduce, the need for applying bleaching compositions to a person's teeth.

The invention also provides compositions and methods for whitening a person's teeth which do not result in increased tooth sensitivity or pain, or which can at least assist in maintaining tooth whiteness while using less bleaching compositions.

The invention further provides compositions and methods for whitening teeth that can increase tooth whiteness above and beyond what is possible using bleaching compositions alone.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A tooth whitening composition comprising:
   a dye capable of reflecting at least one color of light within a portion of the visible spectrum in a range from violet to blue-violet and which is complementary to an initial color of light reflected by a person's tooth such that absorption of the dye by the person's tooth results in the tooth reflecting a color that is perceived to be whiter than the initial color of light reflected by the person's tooth; and
   a carrier.

2. A tooth whitening composition as defined in claim 1, further including a tooth bleaching agent.

3. A tooth whitening composition as defined in claim 2, wherein the tooth bleaching agent comprises a peroxide.

4. A tooth whitening composition as defined in claim 1, wherein the dye comprises a mixture of violet dye and blue dye in which the violet dye predominates.

5. A tooth whitening composition as defined in claim 1, wherein the carrier includes a hydrophilic solvent.

6. A tooth whitening composition as defined in claim 5, wherein the hydrophilic solvent is selected from the group consisting of water, glycerin, alcohols, polyhydric alcohols, polyols, ketones, aldehydes, carboxylic acids, carboxylic acid salts, amines and mixtures thereof.

7. A tooth whitening composition as defined in claim 1, wherein the carrier further includes a gelling agent.

8. A tooth whitening composition as defined in claim 7, wherein the gelling agent is selected from the group consisting of polycarboxylic acids, polycarboxylic acid salts, polysaccharides, polysaccharide derivatives, proteins, protein derivatives, polyalkylene oxides, fumed silica, and mixtures thereof.

9. A tooth whitening composition as defined in claim 1, wherein the tooth whitening composition comprises a toothpaste adapted for use with a toothbrush.

10. A tooth whitening composition as defined in claim 1, wherein the tooth whitening composition is adapted for direct application onto a person's teeth.

11. A method for whitening teeth comprising:
(a) contacting at least one tooth of a person with a tooth whitening composition that includes (i) a dye that reflects at least one color of light within a portion of the visible spectrum in a range from violet to blue-violet and that is complementary to the initial color of light reflected by the person's tooth such that absorption of the dye by the person's tooth results in the tooth reflecting a color that is perceived to be whiter than the initial color of light reflected by the person's tooth and (ii) a carrier;
(b) allowing the tooth whitening composition to remain in contact with the person's tooth for a desired time period in order for a portion of the dye to be absorbed by the person's tooth; and
(c) removing excess dye from the person's tooth.

12. A method for whitening teeth as defined in claim 11, wherein the tooth whitening composition comprises a toothpaste adapted for use with a toothbrush wherein at least step (a) is carried out by brushing the tooth whitening composition over at least one tooth using a toothbrush and wherein step (c) is carried out, at least in part, by rinsing the tooth with water.

13. A method for whitening teeth as defined in claim 11, wherein the tooth whitening composition is substantially abrasiveless, and wherein step (a) is carried out by directly applying the whitening composition to the at least one tooth.

14. A method for whitening teeth as defined in claim 13, wherein the tooth whitening composition is applied to the at least one tooth by means of a cotton swab.

15. A method for whitening teeth as defined in claim 13, wherein the tooth whitening composition is applied to the at least one tooth by means of a syringe.

16. A method for whitening teeth as defined in claim 11, further including bleaching the at least one tooth in addition to contacting the tooth with the tooth whitening composition.

17. A method for whitening teeth as defined in claim 16, wherein bleaching is carried out in a step that is separate from the step of contacting at least one tooth with the whitening composition.

18. A system for whitening teeth comprising:
a tooth whitening composition that includes (i) a dye that reflects at least one color of light within a portion of the visible spectrum in a range from violet to blue-violet and that is complementary to the initial color of light reflected by a person's tooth such that absorption of the dye by the person's tooth results in the tooth reflecting a color that is perceived to be whiter than the initial color of light reflected by the person's tooth and (ii) a carrier; and
an applicator for applying the tooth whitening composition to at least one of the person's teeth.

19. A system for whitening teeth as defined in claim 18, wherein the applicator is selected from the group consisting of a toothbrush, a syringe, and a cotton swab.

20. A system for whitening teeth as defined in claim 18, further including a dental bleaching composition.

* * * * *